United States Patent
Belson

(10) Patent No.: US 8,690,833 B2
(45) Date of Patent: Apr. 8, 2014

(54) INTRAVENOUS CATHETER AND INSERTION DEVICE WITH REDUCED BLOOD SPATTER

(75) Inventor: Ami Belson, Los Altos, CA (US)

(73) Assignee: Vascular Pathways, Inc., Naples, FL (US)

( * ) Notice: Subject to any disclaimer, the term of this patent is extended or adjusted under 35 U.S.C. 154(b) by 31 days.

(21) Appl. No.: 13/358,099

(22) Filed: Jan. 25, 2012

(65) Prior Publication Data

US 2012/0197200 A1 Aug. 2, 2012

Related U.S. Application Data

(60) Provisional application No. 61/438,197, filed on Jan. 31, 2011.

(51) Int. Cl.
*A61M 5/178* (2006.01)
*A61M 31/00* (2006.01)

(52) U.S. Cl.
USPC .................. 604/167.02; 604/164.13; 604/508; 604/510

(58) Field of Classification Search
USPC ............. 604/164.01–166.01, 167.01–167.05, 604/168.01, 508, 510
See application file for complete search history.

(56) References Cited

U.S. PATENT DOCUMENTS

| | | | |
|---|---|---|---|
| 4,177,809 A | 12/1979 | Moorehead | |
| 4,509,534 A | 4/1985 | Tassin, Jr. | |
| 4,585,440 A | 4/1986 | Tchervenkov et al. | |
| 5,084,023 A | 1/1992 | Lemieux | |
| 5,154,703 A | 10/1992 | Bonaldo | |
| 5,531,713 A * | 7/1996 | Mastronardi et al. | 604/263 |
| 5,704,914 A * | 1/1998 | Stocking et al. | 604/164.07 |
| 2005/0075606 A1* | 4/2005 | Botich et al. | 604/110 |
| 2008/0300574 A1* | 12/2008 | Belson et al. | 604/510 |
| 2010/0094310 A1 | 4/2010 | Warring et al. | |
| 2010/0204675 A1* | 8/2010 | Woehr et al. | 604/500 |
| 2010/0210934 A1 | 8/2010 | Belson | |

OTHER PUBLICATIONS

International search report and written opinion dated Apr. 2, 2012 for PCT/US2012/023192.

* cited by examiner

*Primary Examiner* — Aarti Bhatia Berdichevsky
*Assistant Examiner* — Leah Stohr
(74) *Attorney, Agent, or Firm* — Wilson Sonsini Goodrich & Rosati

(57) ABSTRACT

An venous access catheter is combined with a needle, guidewire, and actuator where the needle is disposed coaxially over the guidewire and the catheter is disposed coaxially over the needle. A hub at a proximal end of the access catheter includes a wiping element to clean blood from the needle and guidewire as they are removed and a side port to allow connection of fluids after the access catheter is placed.

30 Claims, 10 Drawing Sheets

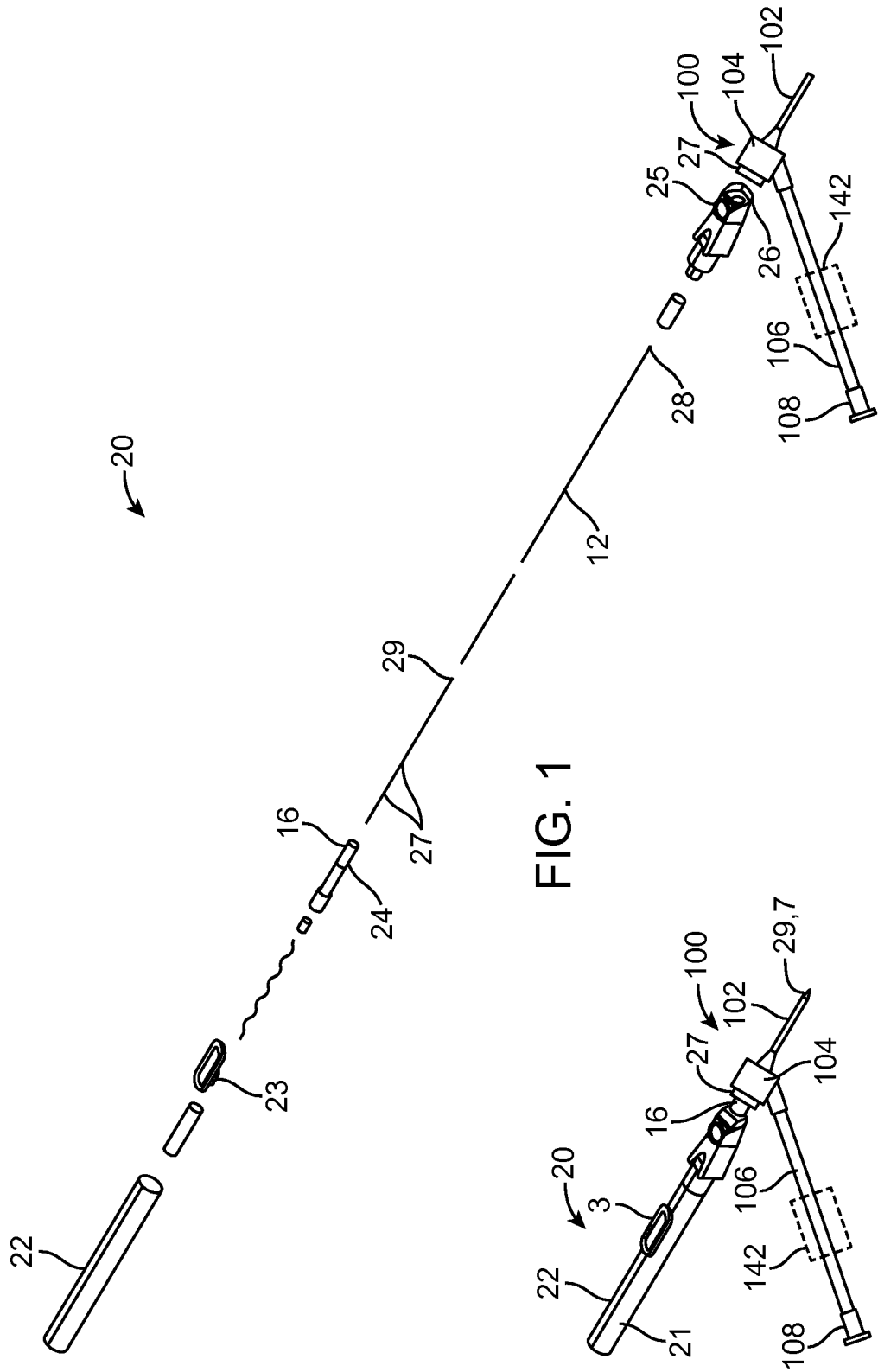

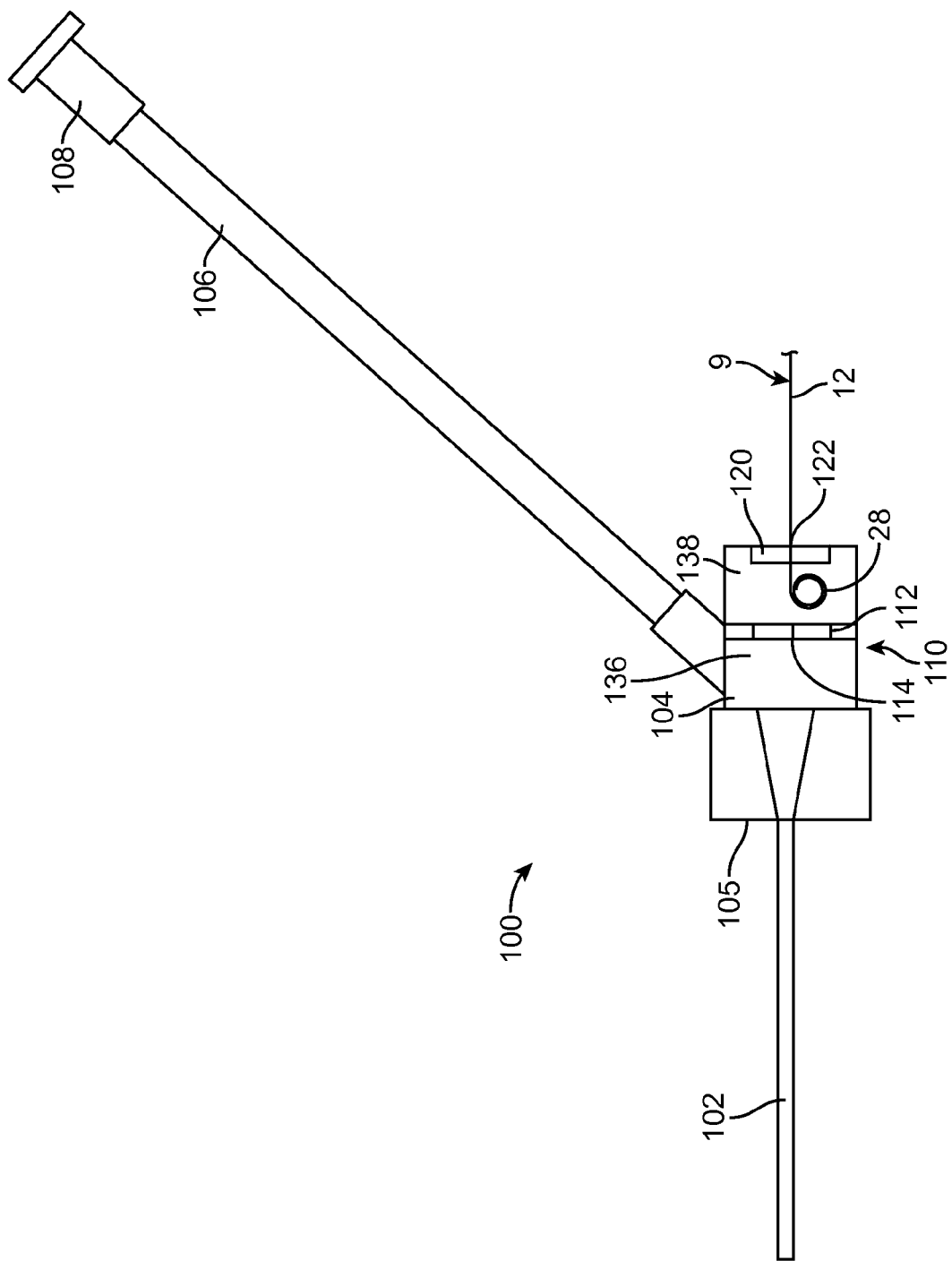

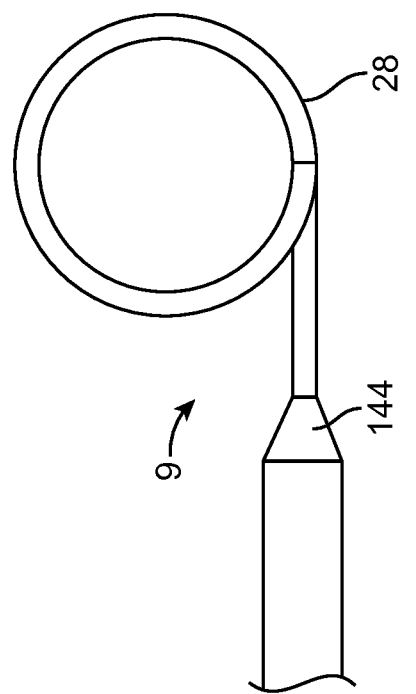
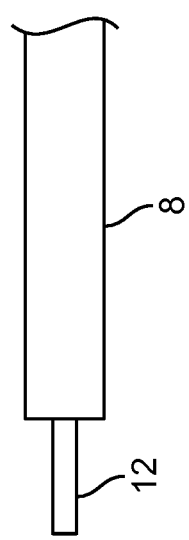
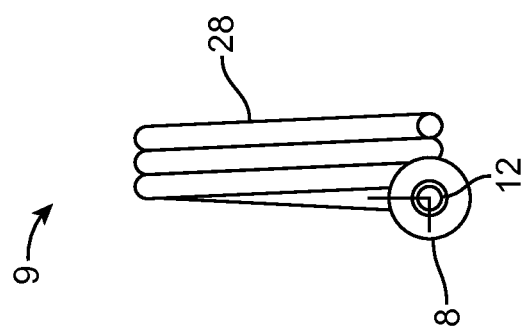
FIG. 11
FIG. 10

INTRAVENOUS CATHETER AND INSERTION DEVICE WITH REDUCED BLOOD SPATTER

This application claims the benefit of provisional application 61/438,197, filed Jan. 31, 2011, the full disclosure of which is incorporated herein by reference.

BACKGROUND OF THE INVENTION

1. Field of the Invention

The present invention relates to devices and methods for insertion and placement of an access catheter into a vein or artery of a patient over a guidewire.

Safe placement of an access catheter into the patient's vein or artery is particularly difficult in the case of small, tortuous, collapsed, fragile, and/or difficult to locate vessels. The risk of accidental punctures and/or contamination by the needle after placement of an intravenous catheter is a particular problem. It is therefore of interest to provide devices and methods which protect medical personnel from potential exposure to blood from the movement of the retracting guidewire.

Of particular interest to the present invention, access catheters are often pre-packaged with both a needle and a guidewire where the needle is coaxially received over the guidewire and the catheter is coaxially received over the needle. The needle extends just beyond the distal tip of the catheter so that the assembly of the needle and catheter can be introduced into the vein or other vessel. As soon as entry into the vein is detected, typically by observing flashback, the guidewire can be advanced into the venous lumen, the catheter advanced over the guidewire, and both the needle and guidewire then removed from the catheter, leaving the catheter available for attachment to sources of fluids, drugs or other intravenous materials.

Removal of the needle and guidewire can be problematic as they have a tendency to carry patient blood and risk the treating personnel to exposure. This can be a particular problem in the case of guidewires having a helical or other shaped tip, such as those described in at least some of the published U.S. patent applications listed below.

For these reasons, it would be desirable to provide systems and methods for use with intravenous and other vascular access catheters to reduce the risk of blood loss and spattering where guidewires and/or needles are withdrawn from the catheter after placement. It would be particularly desirable if such methods and devices were compatible with venous catheters having automatic needle and guidewire retraction mechanisms, as described in the patent publications listed below. At least some of these objectives will be met by the invention as described herein.

2. Background Art

The subject matter of the present invention is related to the following U.S. patent applications, the disclosures of which are hereby incorporated by reference in their entirety. Each of the various embodiments of an intravenous catheter insertion device described in these patent applications can be combined with the intravenous catheter of the present invention to create an intravenous catheter system.

US 20100210934 Intravenous catheter insertion and blood sample devices and method of use
US 20100094310 Intravenous catheter insertion device and method of use
US 20080300574 Intravenous catheter insertion device and method of use Also of interest are the following U.S. patents that describe catheters having sidearm connectors: U.S. Pat. Nos. 5,704,914; 5,154,703; 5,084,023; 4,585,440; 4,509,534; and 4,177,809.

BRIEF SUMMARY OF THE INVENTION

The present invention provides venous and other vascular access catheters which are adapted to reduce the loss and spattering of blood upon withdrawal of needles and guidewires used to introduce the catheters. In particular, the present invention provides a catheter insertion device comprising an access catheter, a needle, a safety guidewire, and an actuator mechanism for selectively advancing the safety guidewire through the needle and selectively withdrawing both the needle and the safety guidewire from the catheter at desired points in the catheter insertion protocol. The present invention provides a chamber and a septum or other membrane as a "wiping" element on a proximal hub, housing, or other component of the access catheter. The chamber is preferably disposed at a proximal end of a hub having an interior chamber spaced apart from a proximal end of the catheter. A septum is preferably disposed on a proximal side of the chamber to wipe residual blood from the guidewire as the guidewire is withdrawn by the actuator. An insertion tool for the needle and/or guidewire is removably attached to the hub adjacent the septum so that the needle and guidewire may be advanced through the septum and into the catheter for selective advancement in order to permit introduction of the catheter into an artery or vein in a generally conventional manner. The actuator is further adapted to withdraw the needle and guidewire, typically under the force of a spring or other biasing element which rapidly withdraws the needle and catheter into and through the interior of the hub. Usually, the guidewire will be a "safety" guidewire having a helical or other preformed atraumatic shape at its distal end which is assumed when the safety guidewire exists from a distal tip of the needle in order to reduce the risk of damaging the vessel as the guidewire is advanced. As the guidewire is withdrawn, the safety tip will be straightened as it passes through the needle lumen and will resume the helical or other configuration within the interior of the hub, thus being able to shed blood which it may have picked up while in the artery or vein into the hub rather than into the surrounding tissue or housing. The guidewire can then be further withdrawn through the septum in order to remove any remaining blood before it is drawn back into the actuator for safe disposal. A side port, typically with a side tube, is provided on the hub in order to introduce desired fluids in order to accommodate the septum or other wiping element which is present on the proximal end of the hub.

BRIEF DESCRIPTION OF THE DRAWINGS

FIG. 1 shows an exploded view of an intravenous catheter and insertion device according to the present invention.

FIG. 2 shows an assembly drawing of the intravenous catheter and insertion device in an undeployed state, ready for use.

FIG. 9 is an enlarged view of another embodiment of an intravenous catheter according to the present invention.

FIGS. 10 and 11 illustrate another embodiment of a guidewire for use with the intravenous catheter and insertion device. FIG. 10 is a proximal end view of the guidewire, and FIG. 11 is a side view of the guidewire.

DETAILED DESCRIPTION OF THE INVENTION

Figure 3:
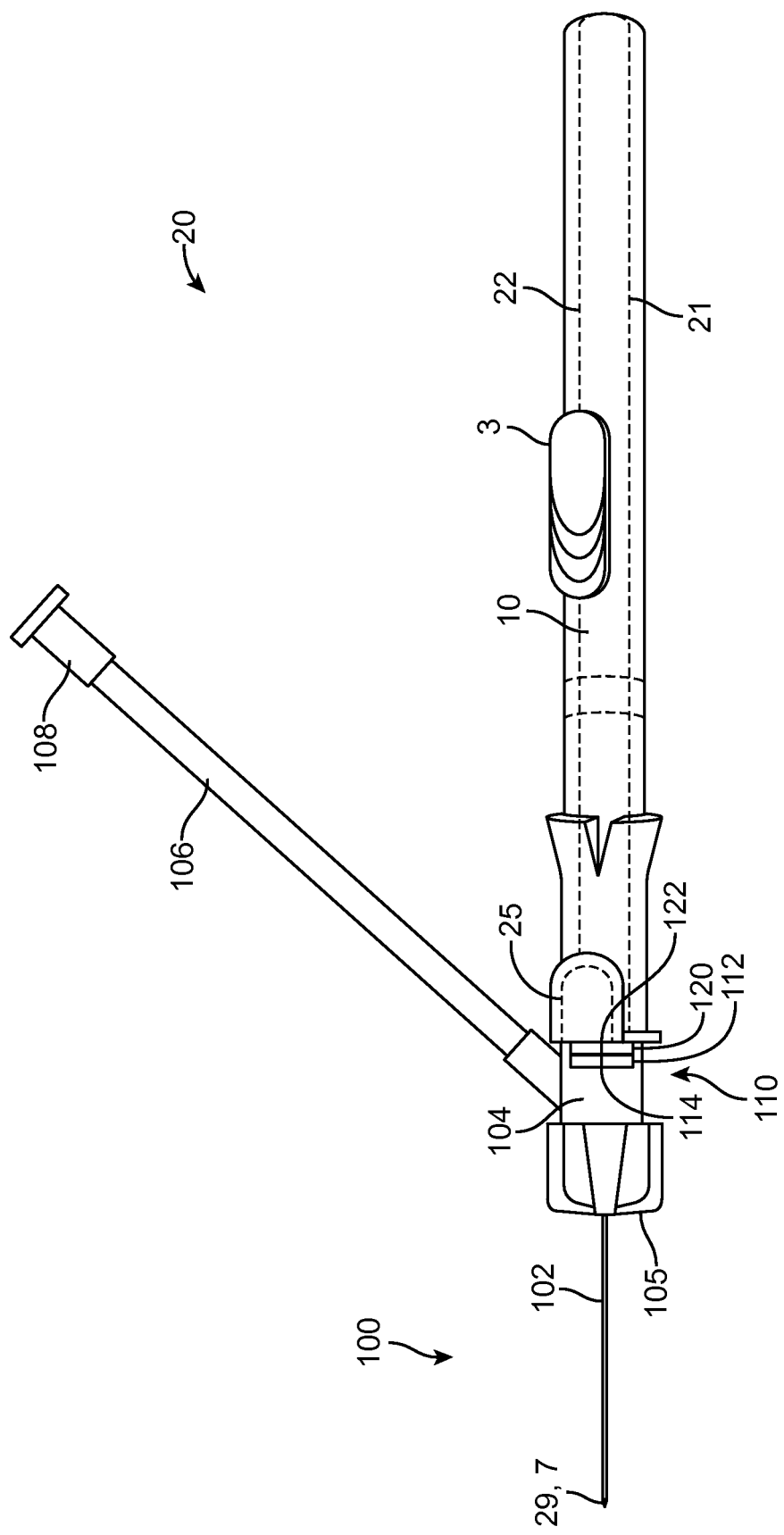
FIG. 3 shows an intravenous catheter and insertion device in an undeployed state, ready for use.

FIG. 1 shows an exploded view of one embodiment of an intravenous catheter 100 and insertion device 20 according to the present invention. FIG. 2 shows an assembly drawing of the intravenous catheter 100 and insertion device 20 in an undeployed state, ready for use. Additional intravenous catheter insertion devices that can be used in the present invention are described in detail in the following patent applications: US 20100210934, US 20100094310 and US 20080300574, which have been incorporated by reference.

The intravenous catheter insertion device 20 has a housing 21, which includes a proximal housing 1 that is adhesively joined or otherwise connected to a distal housing 11. In the example shown, the proximal housing 1 is in the form of an elongated hollow cylinder. The distal housing 11 is optionally formed in an ergonomic handle shape designed to be held by the thumb and forefinger of a user. Other shapes are also possible. The housing 21 has an elongated slot 22 that extends from the proximal housing 1 to the distal housing 11 approximately parallel with a longitudinal axis of the housing 21. A wire advance slider 3 slides in a longitudinal direction along an exterior of the proximal housing 1 and the distal housing 11 and has a tongue 23 that extends through the slot 22 into the interior of the housing 21. A needle carrier 6 is slidable within the interior of the housing 21 and is positioned distal to the tongue 23 of the wire advance slider 3. The distal end of the needle carrier 6 includes a luer slip fitting 16 or the like. There is a notch 24 in the needle carrier 6 just proximal to the luer slip fitting 16. A button 25 is located on one side of the distal housing 11, which has a tab 26 that is configured to engage the notch 24 in the needle carrier 6 when the needle carrier 6 is in its most distal position. A cylindrical guidewire stop 2 is adhesively bonded into the proximal end of the proximal housing 1.

A tubular stainless steel hypodermic needle 7 with a sharpened, beveled distal end 29 is bonded with adhesive 13 or otherwise attached to the distal end of the needle carrier 6. Preferably, the needle 7 has one or more slots 27 cut into the sides of it connecting to the needle lumen for the passage of blood. A guidewire 9 is bonded with adhesive 14 or otherwise attached to the tongue 23 of the wire advance slider 3. The guidewire 9 is preferably made of a highly resilient material, such as a superelastic Nickel-Titanium alloy wire approximately 0.003-0.012 inches in diameter and most preferably approximately 0.004 inches in diameter. The guidewire 9 may be uniform in diameter or it may be made stepped or tapered in diameter, for example by grinding. For example, a 0.008 inch diameter wire can be centerless ground to create a 0.004 inch diameter distal portion with a short tapered transition. Optionally, a proximal portion of the guidewire 9 may be supported with a support tube 8 made from stainless steel or Nickel-Titanium alloy hypodermic tubing or a molded or extruded polymer tube. Another option for constructing the guidewire 9 would be to join a short distal portion of a highly resilient material, such as a superelastic Nickel-Titanium alloy wire, to a larger diameter, solid or tubular proximal portion, for example by welding, swaging, crimping and/or adhesive bonding. As best seen in FIG. 9, the distal end of the guidewire 9 is preformed into a tightly wound spiral 28 with an outer diameter smaller than the internal diameter of the target vessel into which it will be inserted. The spiral tip 28 acts as a safety bumper on the guidewire 9 to avoid puncturing or damaging the inside of target vessels. The coiled guidewire tip 28 is particularly useful in protecting fragile or delicate veins. Due to the extreme flexibility of the Nickel-Titanium alloy wire, the spiral distal curve 28 can straighten out when the guidewire 9 is withdrawn into the needle 7 and completely recover into the spiral configuration without plastic deformation when the guidewire 9 is advanced out of the needle 7. In the example shown, the distal end of the guidewire 9 has a first, small diameter coil of approximately 0.167 inches in diameter for approximately 0.75 revolutions and a second, larger diameter coil of approximately 0.175 inches in diameter for approximately 1 revolution. The first and second coils are preferably approximately coplanar with one another and preferably approximately coplanar with the straight proximal portion 12 of the guidewire 9 also. Other configurations of the guidewire 9 may include: multi-planar, single coil, full radius on the end, and/or a balled end with a diameter less than the diameter of the needle.

The guidewire 9 is positioned to move coaxially through the lumen of the needle 7. Optionally, a flexible tether 4 connects from the tongue 23 of the wire advance slider 3 to the proximal end of the needle carrier 6. Optionally, a needle carrier cap 5 may be provided to facilitate adhesively attaching the tether 4 to the proximal end of the needle carrier 6. The length of the tether 4 prevents the guidewire 9 from being withdrawn too far proximally with respect to the needle 7 because the small-diameter distal coil 28 would be difficult to reinsert into the proximal end of the needle 7 if it were to be completely withdrawn from the needle lumen. In another option, instead of using a tether, a plastic protrusion or another physical structure, such as a gate, can act as a detent to block the guidewire 9 from withdrawing beyond the desired point. Optionally, the detent may be configured so that it can be overrun when a forceful retraction occurs, such as the one that is initiated by the spring 10, thus allowing complete retraction of the guidewire 9. In another option, the housing 21 may be configured such that the guidewire 9 or the structure that is connected to the guidewire 9 will hit a positive stop, such as the guidewire stop 2 or the proximal end of the housing 21, before the guidewire 9 gets to a position too proximal relative to the needle 6.

The proximal housing 1, distal housing 11, wire advance slider 3, button 25, needle carrier 6, guidewire stop 2 and needle carrier cap 5 may be formed from any material suited for use in medical applications. For example, some or all of these parts may be molded and/or machined from a rigid, transparent medical grade plastic, such as acrylic or polycarbonate.

A compression spring 10 or similar biasing member is positioned between the needle carrier 6 and the distal end of the housing 21 to urge the needle carrier 6 in a proximal direction. The force of the spring 10 is resisted by the tab 26 of the button 25, which engages the notch 24 in the needle carrier 6 when the needle carrier 6 is in its most distal position. It should be noted that in FIG. 1 the spring 10 is shown in a compressed condition as it would be in the assembled intravenous catheter insertion device 20 in an undeployed condition.

Figure 6:
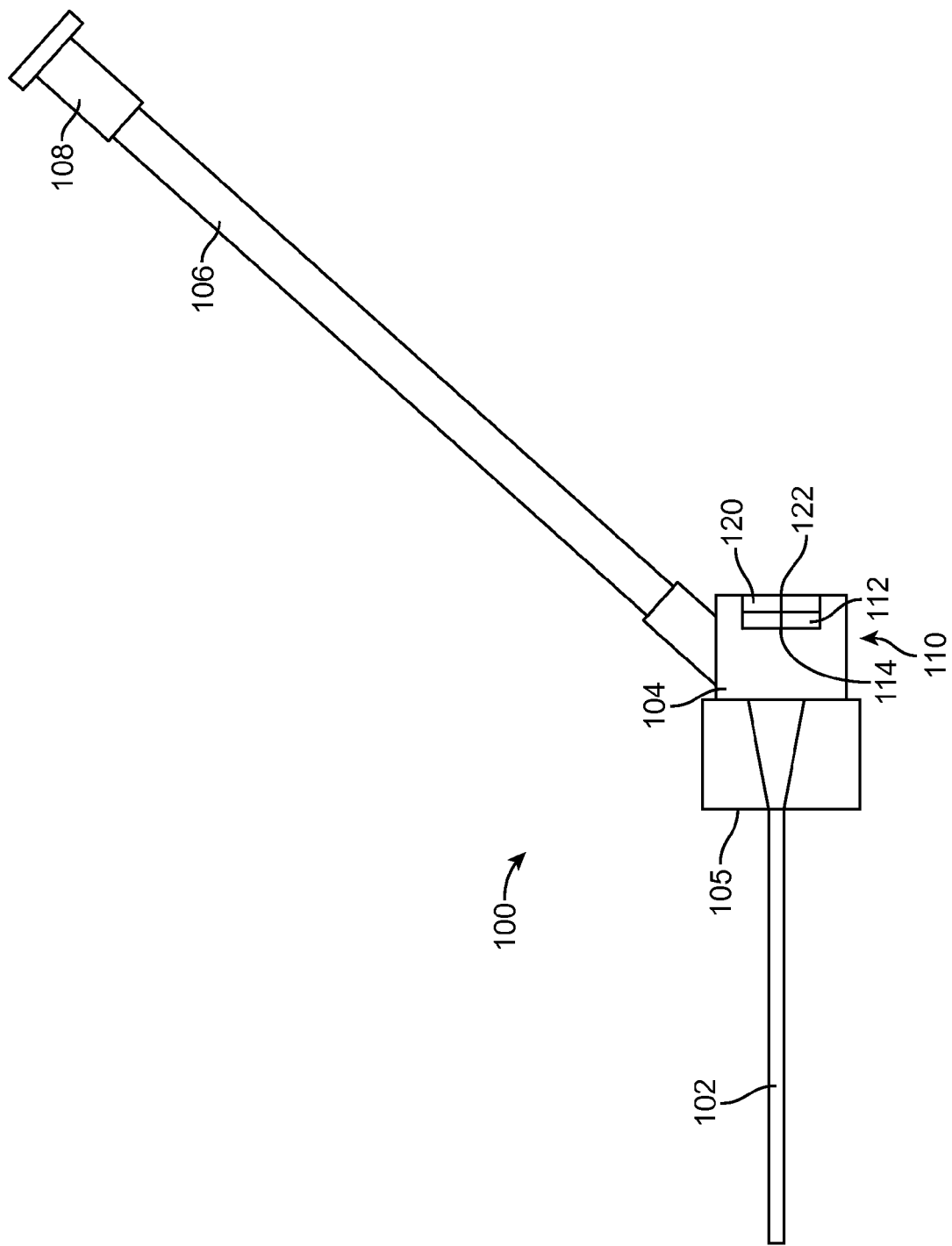
FIG. 6 is an enlarged view of the intravenous catheter of FIG. 3.

The intravenous catheter 100, which is shown in an enlarged view in FIG. 6, has a catheter tube 102 with an inner lumen that fits coaxially around the needle 7 of the insertion device 20. The catheter tube 102 is preferably extruded of a flexible medical grade polymer having a low coefficient of friction, for example PTFE, polypropylene or polyethylene. Preferably, the intravenous catheter tube 102 has a close fit with the needle 7 and a tapered distal end to minimize any step between the needle 7 and the catheter tube 102 as they are inserted through the wall of a vein.

The proximal end of the catheter tube 102 is connected to a proximal fitting 104 that connects to the distal end of a flexible sidearm tube 106, which extends laterally from the side of the proximal fitting 104. Preferably, the proximal fitting 104 is molded of a clear polymer so that blood flashback from the needle 7 can be observed in the proximal fitting 104. A luer fitting 108 or the like is attached to the proximal end of the sidearm tube 106. A fluid flow path is formed from the luer fitting 108 through the sidearm tube 106 to the proximal fitting 104 and the catheter tube 102. Preferably, the fluid flow path is free of obstructions, sudden changes of diameter or dead spaces that would interfere with fluid flow or be a nidus for thrombus formation. Optionally, the intravenous catheter 100 may include wings 105, which facilitate taping the intravenous catheter 100 to the patient's skin after insertion. The wings 105 may be rigid or flexible and, optionally, may be molded integrally with the proximal fitting 104.

A hemostasis valve 110 is located on a proximal side of the proximal fitting 104. The hemostasis valve 110 is preferably configured as an elastomeric membrane 112 with a small hole 114 at the center of the elastomeric membrane 112. The hole 114 forms a sliding seal around the needle 7 of the insertion device 20. Alternatively, the elastomeric membrane 112 may be intact and the needle 7 will form a hole 114 as it is inserted through the membrane 112. The elastomeric membrane 112 can be made of latex, silicone, polyurethane or another medical grade elastomer. Optionally, a small amount of medical grade lubricant, such as silicone oil, may be used to reduce the friction of the needle 7 passing through the hemostasis valve 110. Other configurations of hemostasis valves known in the industry, such as those having different configurations of membranes, holes, slits or duckbill valves, may also be used. Optionally, more than one or a combination of different hemostasis valves 110 may be used.

Optionally, located proximal to the hemostasis valve 110 is a wiping element 120. The wiping element 120 is adapted to remove blood from the surface of the guidewire 9 and needle 7 as they are withdrawn from the intravenous catheter 100. The wiping element 120 may be made of an absorbent or superabsorbent material to absorb blood from the surface of the needle 7 and guidewire 9. Examples of suitable materials include, but are not limited to, cotton wool, gauze, felt, natural or artificial sponge, open-cell foam, etc. Alternatively, the wiping element 120 may be configured as an elastomeric membrane that acts like a squeegee to remove blood from the surface of the guidewire 9. The elastomeric membrane will preferably be sufficiently elastic to adapt to the larger diameter of the needle 7 and then to the smaller diameter of the guidewire 9 when the needle 6 has been withdrawn. Preferably, the wiping element 120 is made with a hole or slit 122 in the center that is aligned with the hole 114 in the hemostasis valve 110. Alternatively, the wiping element 120 may be intact and the needle 7 will form a hole 122 as it is inserted through the wiping element 120.

Optionally, there may be a luer fitting 27 or the like on the proximal fitting 104 of the intravenous catheter 100 that fits onto a luer slip fitting 16 on the distal end of the needle carrier 6 with a slight interference fit to hold the intravenous catheter 100 in place, as shown in FIGS. 1 and 2. Alternative configurations of the device may use a luer lock or other locking mechanism to temporarily attach the intravenous catheter 100 to the insertion device 20. Alternatively, the friction of the needle 7 passing though the hemostasis valve 110 and wiping element 120 may be sufficient to hold the intravenous catheter 100 onto the insertion device 20.

An optional feature of the intravenous catheter 100 in any of the embodiments described herein is a means 142 for selectively blocking or occluding fluid flow through the flexible sidearm tube 106. This can be in the form of a tubing clamp or stopcock located on the flexible sidearm tube 106 or on the luer fitting 108, as shown in FIGS. 1 and 2. Alternatively, a separate stopcock can be connected to the luer fitting 108 for selectively blocking fluid flow.

Figure 4:
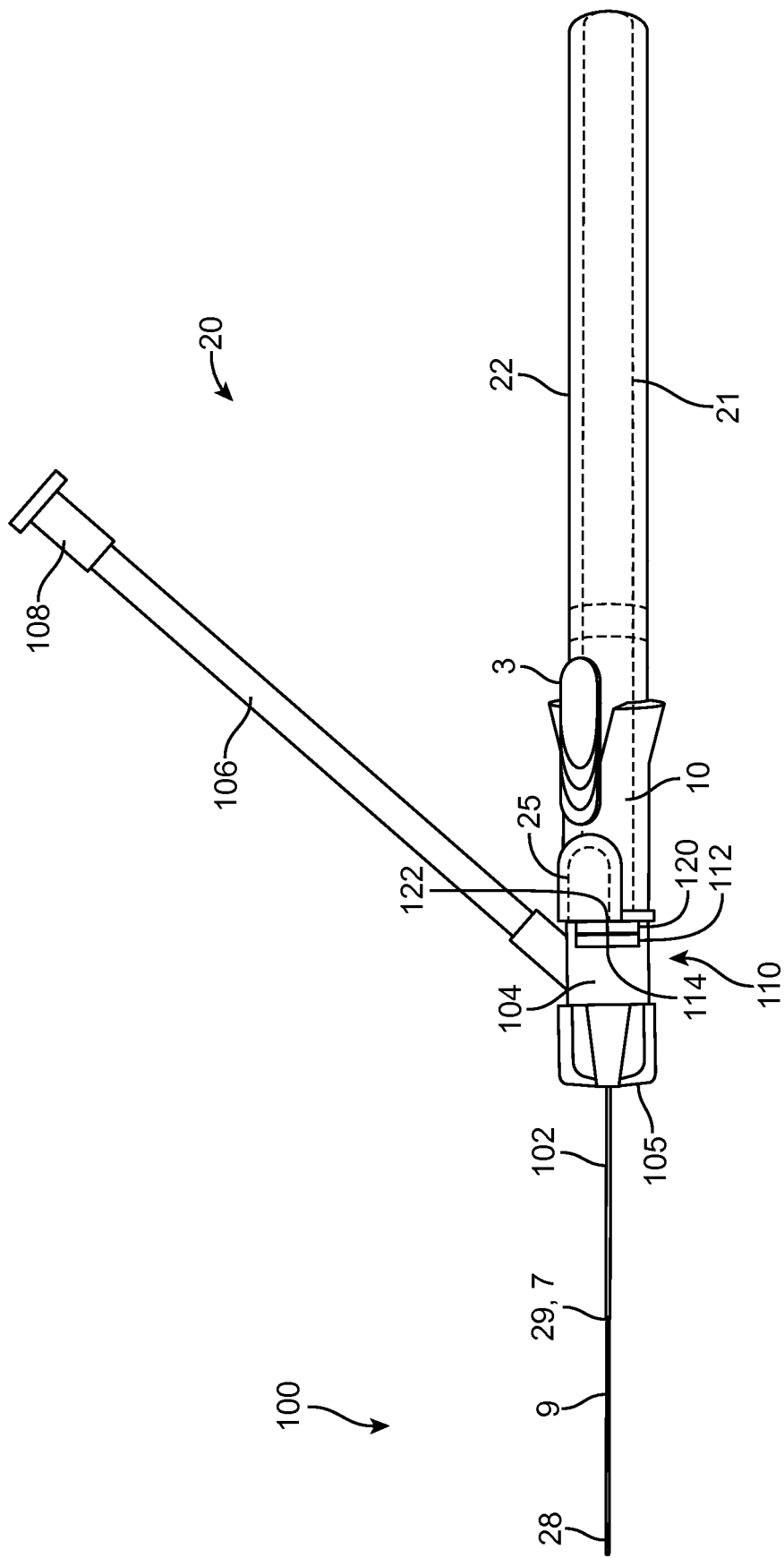
FIG. 4 shows the intravenous catheter and insertion device of FIG. 3 with the guidewire advanced.
Figure 5:
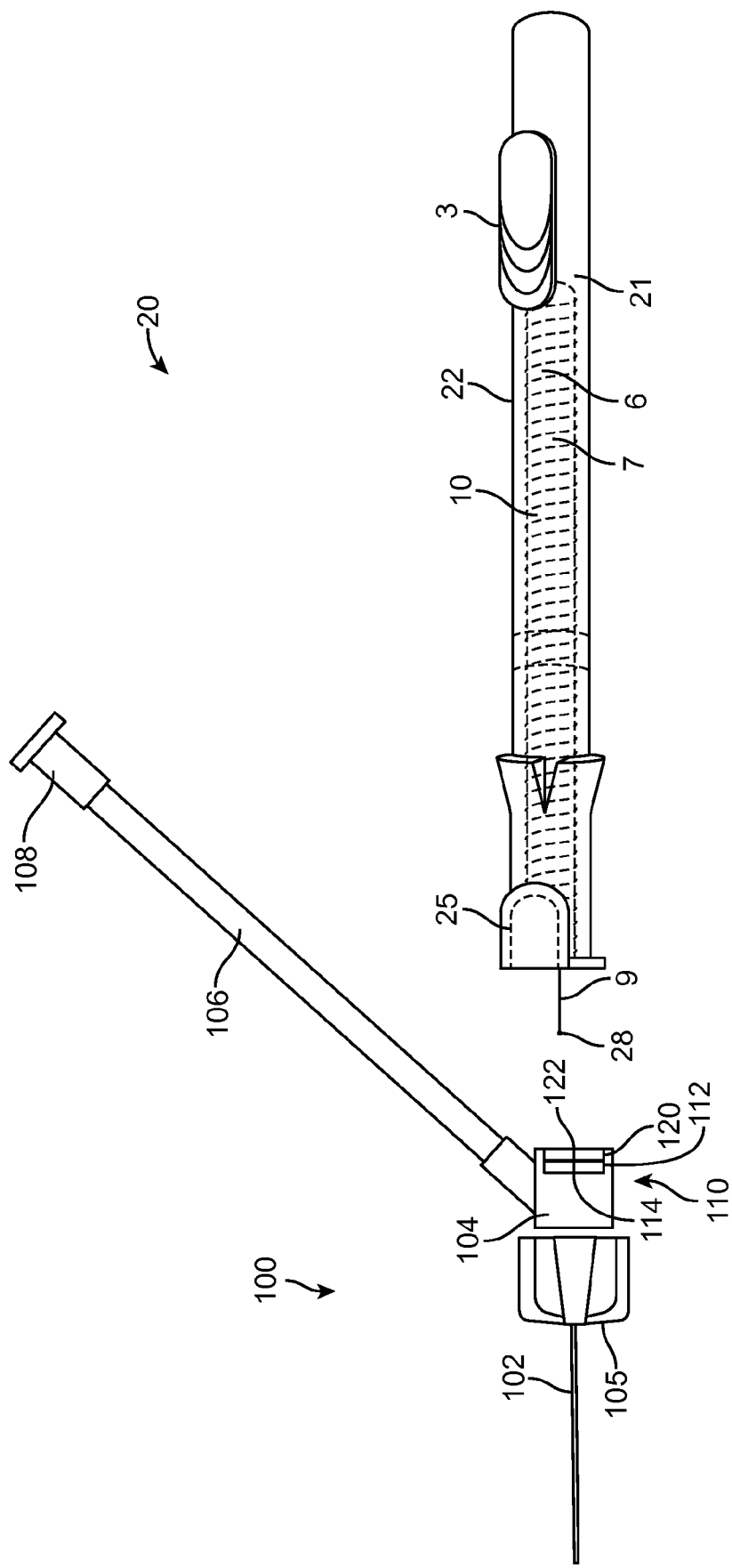
FIG. 5 shows the intravenous catheter and insertion device of FIG. 3 with the guidewire and needle retracted.

FIGS. 3-5 illustrate steps in a method of inserting an intravenous catheter 100 using an intravenous catheter insertion device 20, such as those described above in connection with FIGS. 1, 2 and 6. The intravenous catheter 100 and insertion device 20 are provided as a single-use, non-reusable device supplied to the physician or other medical practitioner sterile in a ready-to-use, undeployed condition, as shown in FIG. 3. In another option, the device can be stored with the distal spiral portion 28 of the guidewire 9 advanced distally from the tip of the needle 7 so that it is not straightened during storage. In this case, the operator will fully retract the guidewire 9 into the needle 7 before use. In use, the operator uses the housing 21 as a handle to manipulate the intravenous catheter 100 and insertion device 20. With the device in the undeployed condition, the needle 7 is used to puncture a vein. When venous blood is observed in the proximal fitting 104, the operator knows that the distal tip of the needle 7, together with the distal part of the catheter tubing 102, is in the lumen of the vein. The operator can then advance the slider 3 in the distal direction to extend the guidewire 9 out of the needle 7 into the lumen of the vein, as shown in FIG. 4. The distal portion of the guidewire 9 assumes its spiral configuration 28 to act as a safety bumper to prevent accidental puncture of the far wall of the vein or other damage to the vein and also to enable passage along obstructions such as valves or curves. With the guidewire 9 thus deployed, the operator can safely continue advancing the intravenous catheter 100 until it is inserted far enough into the vein, then the operator pushes the button 25, which disengages the tab 26 from the notch 24 in the needle carrier 6. The spring 10 urges the needle carrier 6 and the slider 3 in the proximal direction, thus simultaneously withdrawing the needle 7 and the guidewire 9 into the housing 21, leaving only the intravenous catheter 100 in the lumen of the vein. FIG. 5 shows the insertion device 20 with the needle 7 and the guidewire 9 withdrawn into the housing 21. Preferably, the coil 28 on the distal tip of the guidewire 9 is visible when the insertion device 20 is in the deployed position, as shown in FIG. 5. This allows the operator to verify that the guidewire 9 is intact and that only the intravenous catheter 100 has been left in the patient's vein.

While it is desirable for the insertion device 20 to withdraw the needle 7 and the guidewire 9 simultaneously, the actuator mechanism could also be modified to withdraw the needle 7 and the guidewire 9 sequentially. For example, the actuator mechanism could withdraw the needle 7 first and then, after a slight delay, withdraw the guidewire 9. Alternatively, the actuator mechanism could be modified to require two separate motions of one actuator member or selective movements of two separate actuator members to withdraw the needle 7 and the guidewire 9 selectively. As another alternative, the spring 10 may be omitted from the actuator mechanism, thus allowing the needle 7 and the guidewire 9 to be withdrawn manually using the slider 3. Once the intravenous catheter 100 has been inserted into the patient's vein, the slider 3 is moved proximally along the slot 22 to withdraw the needle 7 and the guidewire 9 into the housing 21.

Figure 7:
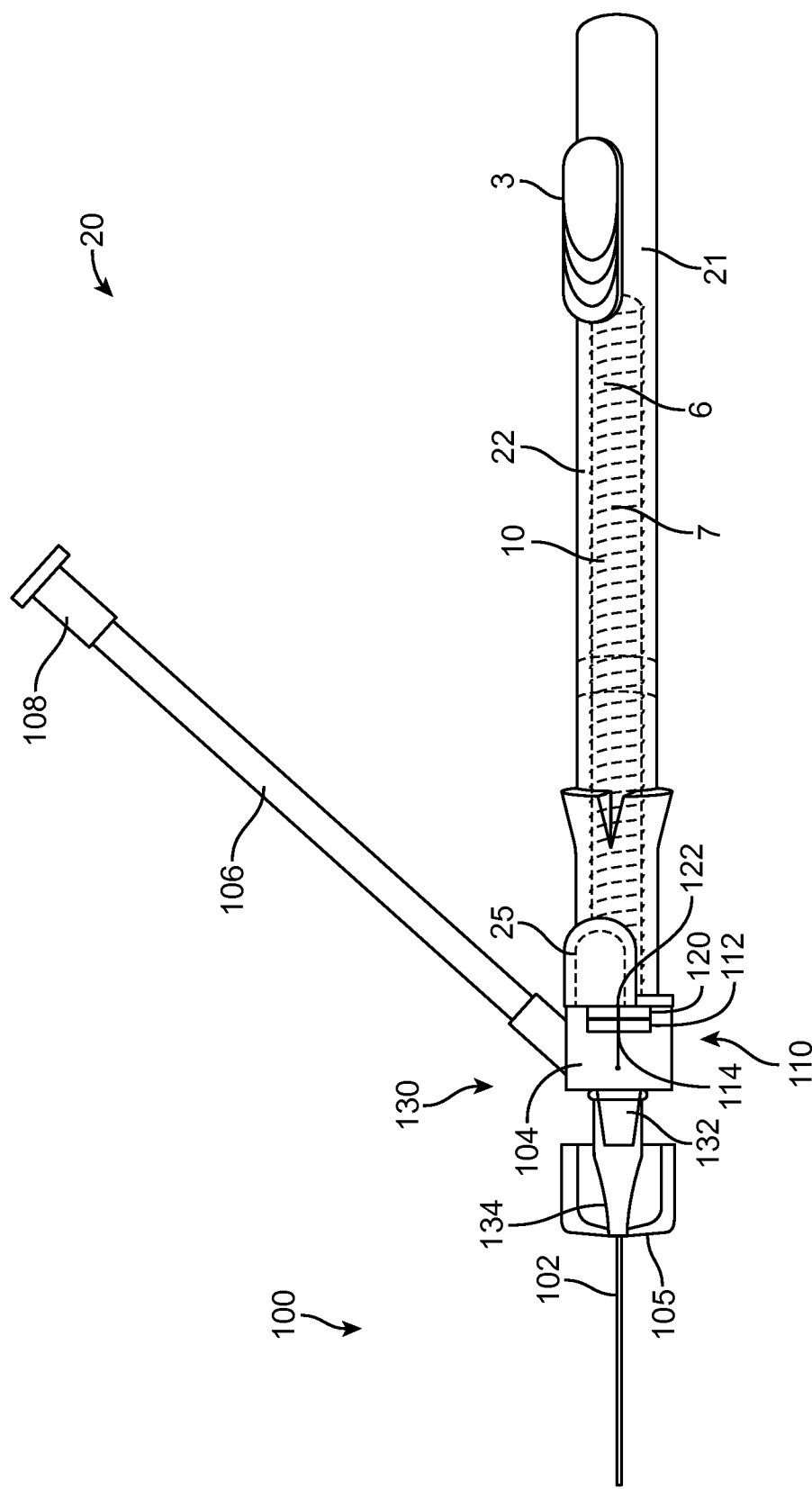
FIG. 7 shows an embodiment of the intravenous catheter and insertion device with a separate sidearm adapter.
Figure 8:
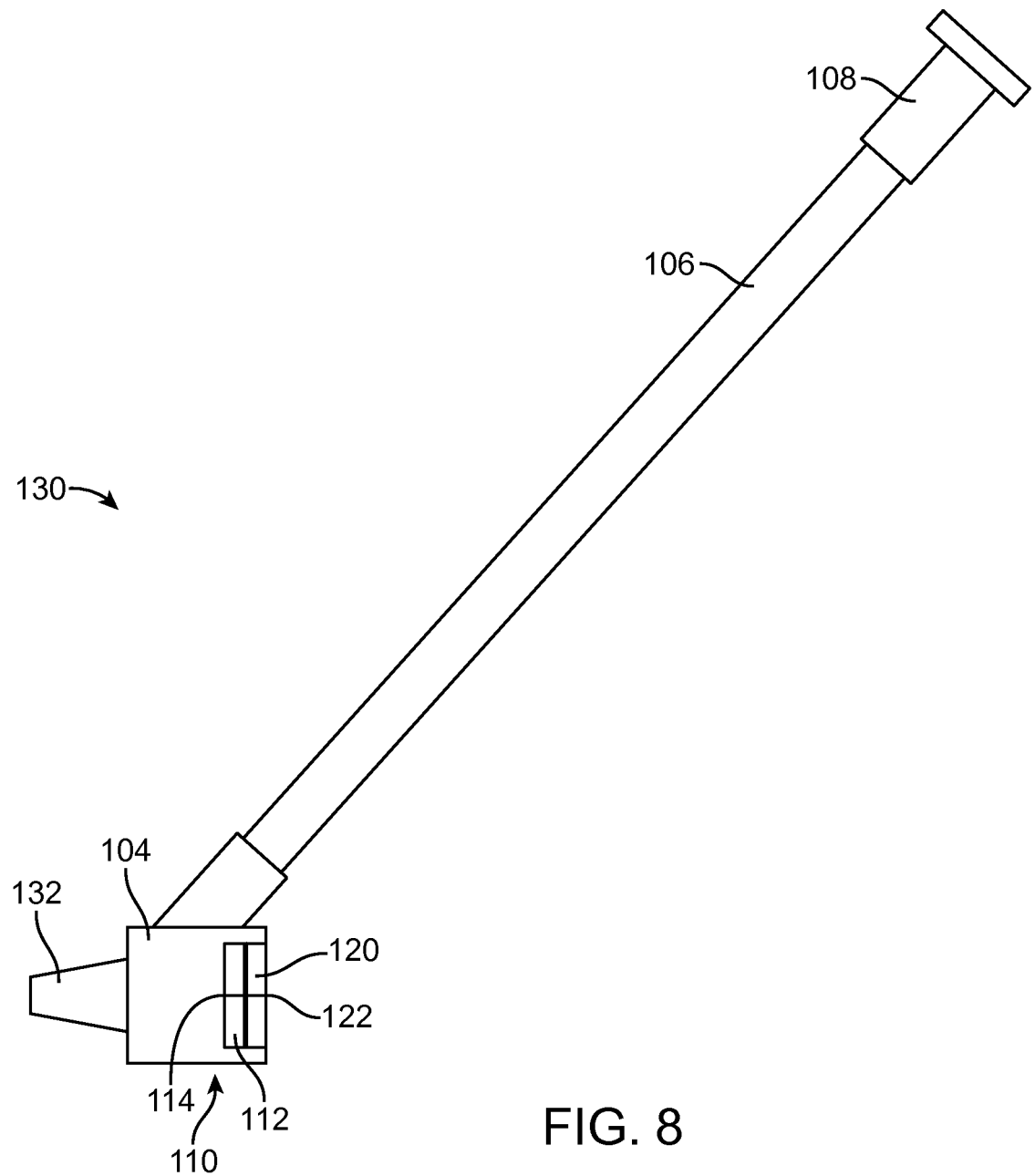
FIG. 8 is an enlarged view of the sidearm adapter of FIG. 7.

FIG. 7 shows an embodiment of the intravenous catheter 100 and insertion device 20 with a separate sidearm adapter 130. FIG. 8 is an enlarged view of the sidearm adapter 130 of FIG. 7. The structure of the intravenous catheter 100 is similar to that described above in connection with FIG. 6, except that the proximal fitting 104 has a male luer connector 132 on its distal end that interlocks with a female luer connector 134 on the proximal end of the catheter tube 102.

FIG. 9 is an enlarged view of another embodiment of an intravenous catheter 100 according to the present invention. The proximal fitting 104 and the sidearm 106 may be integral to the intravenous catheter 100, as shown in FIG. 9, or they may be part of a separate sidearm adapter, similar to that shown in FIGS. 7 and 8. In this embodiment, the proximal fitting 104 has a first chamber 136 in fluid connection with the catheter tube 102 and a second chamber 138 separated from the first chamber 136 by the hemostasis valve 110. Optionally, a wiping element 120 for removing blood from the guidewire 9 is located on the proximal side of the second chamber 138. Preferably, the second chamber 138 is sized to allow the coiled tip 128 of the guidewire 9 to resume its coiled configuration after it is withdrawn through the hemostasis valve 110. Any dripping or spattering of blood from the guidewire 9 will occur in the second chamber 138. The optional wiping element 120 will help to remove any remaining blood from the guidewire 9 as it is withdrawn from the second chamber 138.

FIGS. 10 and 11 illustrate another preferred embodiment of a guidewire 9 for use with the intravenous catheter 100 and insertion device 20 of the present invention. FIG. 10 is a proximal end view of the guidewire 9, and FIG. 11 is a side view of the guidewire 9. The guidewire 9 is preferably made of a highly resilient material, such as a superelastic Nickel-Titanium alloy wire with a uniform diameter of approximately 0.003-0.012 inches and most preferably approximately 0.004 inches. The distal end of the guidewire 9 is preformed into a tightly wound spiral 28 with an outer diameter smaller than the internal diameter of the target vessel into which it will be inserted. Due to the extreme flexibility of the Nickel-Titanium alloy wire, the spiral distal curve 28 can straighten out when the guidewire 9 is withdrawn into the needle 7 and completely recover into the spiral configuration without plastic deformation when the guidewire 9 is advanced out of the needle 7. In the example shown, the spiral distal curve 28 of the guidewire 9 is in the form of a helix with approximately three coils or rotations of substantially uniform diameter. In a particularly preferred embodiment, the helical coils of the spiral distal curve 28 have an outer diameter of approximately 0.052 inches (approximately 1.3 mm). Alternatively, the spiral distal curve 28 may be in the form of a conical helix with coils that diminish or increase in diameter. In the example shown, the helical coils of the spiral distal curve 28 have a central axis that is perpendicular to and offset from an axis defined by the proximal portion 12 of the guidewire 9. In other embodiments, the central axis of the spiral distal curve 28 may be skewed from the axis of the proximal portion 12 of the guidewire 9. Other possible configurations of the spiral distal curve 28 of the guidewire 9 are described in patent applications US 20100210934, US 20100094310 and US 20080300574, which have been incorporated by reference.

The proximal portion 12 of the guidewire 9 is preferably supported with a support tube 8 made from stainless steel or Nickel-Titanium alloy hypodermic tubing or, alternatively, a molded or extruded tube made of a polymer, such as, but not limited to, FEP, PEEK or HDPE. The support tube 8 will preferably have an inner diameter sufficient for the proximal portion 12 of the guidewire 9 to be inserted through it, for example 0.006 inches inner diameter to accommodate a 0.004 inch diameter guidewire 9. The support tube 8 will preferably have an outer diameter of approximately 0.012-0.016 inches and most preferably approximately 0.014 inches. Optionally, the support tube 8 may be adhesively bonded or otherwise attached to the proximal portion 12 of the guidewire 9 with the distal end of the support tube 8 positioned a short distance proximal to the spiral distal curve 28. The support tube 8 may have a tapered distal end 144, which may be formed by a molding process or by applying a filet of adhesive or other material during assembly.

Figure 12:
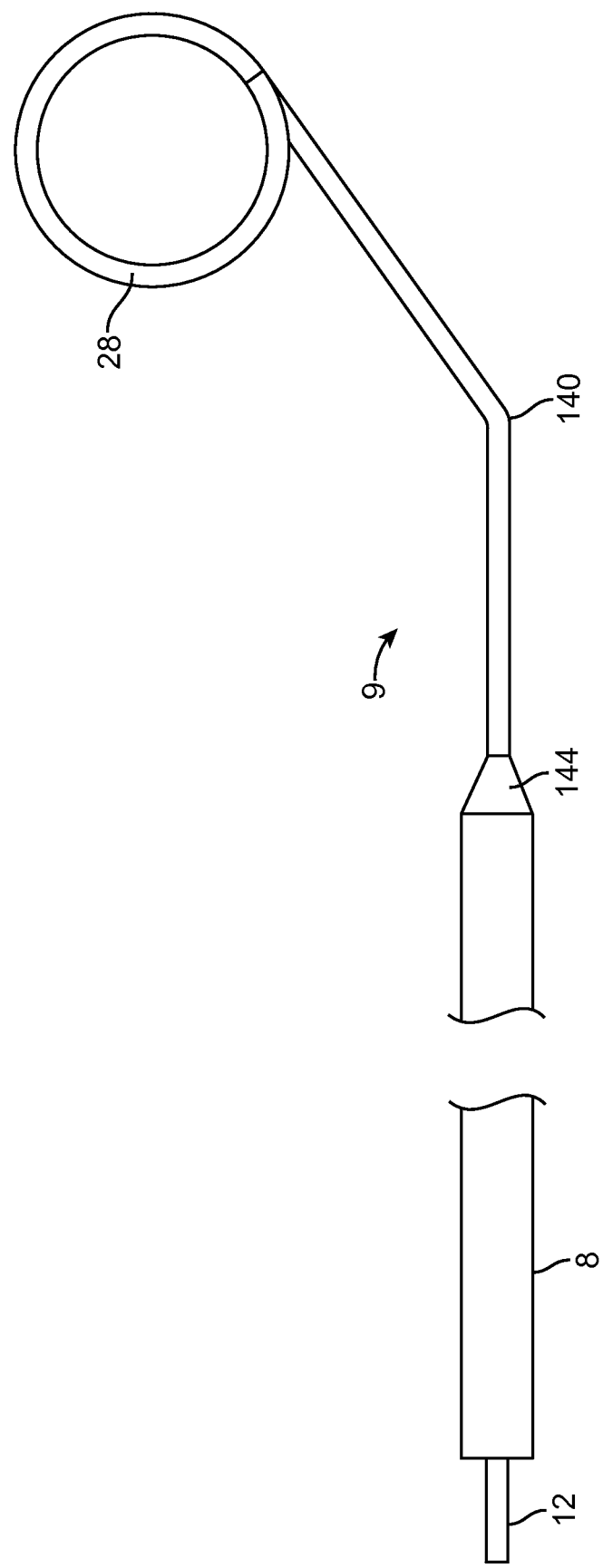
FIG. 12 illustrates an embodiment of a steerable guidewire for use with the intravenous catheter and insertion device.

FIG. 12 illustrates another embodiment of a guidewire 9 for use with the intravenous catheter 100 and insertion device 20 of the present invention. The guidewire 9 may be made from a uniform-diameter wire or a tapered wire and may optional be supported by a support tube 8 as described above. The spiral distal curve 28 of the guidewire 9 may be any of the configurations described or incorporated herein. There is a bend 140 of approximately 30 to 60 degrees in the guidewire 9 a short distance, for example 1 to 5 mm, proximal to the spiral distal curve 28. The bend 140 may be located just at the distal end 144 of the support tube 8 or, optionally, the bend 140 may be located a short distance, for example 1 to 5 mm, distal to the distal end 144 of the support tube 8. The bend 140 allows the guidewire 9 to be used in a steerable fashion to facilitate negotiating tortuous and/or branching blood vessels.

While the present invention has been described herein with respect to the exemplary embodiments and the best mode for practicing the invention, it will be apparent to one of ordinary skill in the art that many modifications, improvements and subcombinations of the various features and embodiments, adaptations and variations can be made to the invention without departing from the spirit and scope thereof.

What is claimed is:

1. A catheter insertion device, comprising:
   an outer housing;
   a tubular access needle attached to a needle carrier, wherein said needle carrier is slidable with respect to said outer housing;
   a tubular catheter having a proximal hub releasable attached at a distal end of said outer housing and positioned coaxially around said tubular access needle, said hub having an interior and a septum, wherein the tubular access needle passes through the septum;
   a safety guidewire sized and configured to be advanced through said tubular access needle;
   a wiping element on a proximal side of the septum, said wiping element being configured to remove blood from surfaces of the tubular access needle and the safety guidewire as they are withdrawn through the septum;
   an actuator mechanism configured to selectively advance said safety guidewire out through said tubular access needle in a distal direction and subsequently to simultaneously withdraw said safety guidewire and said tubular access needle in a proximal direction with respect to said tubular catheter; and
   a blood spatter chamber disposed between the proximal hub of the tubular catheter and the actuator.

2. The catheter insertion device as in claim 1, further comprising a sidearm connector connected to the hub to receive blood from the interior when the needle has been withdrawn through the septum.

3. The catheter insertion device of claim 1, wherein the guidewire has a coiled tip and the blood spatter chamber is sized to allow the coiled tip to resume its coiled configuration as the guidewire is withdrawn by the actuator.

4. The catheter insertion device as in claim 1, wherein said actuator mechanism compresses a compression spring located at a distal end of the housing coaxially over the tubular access needle and safety guidewire and an interlock which can be selectively released to allow the compression spring to elongate to simultaneously withdraw said safety guidewire and said tubular access needle.

5. The catheter insertion device of claim 1, further comprising: an actuator handle configured to move distally with respect to said outer housing to selectively advance said safety guidewire out through said tubular access needle in a distal direction, wherein said actuator handle is configured to rotate laterally to actuate an interlock to allow withdrawal of said safety guidewire and said tubular access needle in a proximal direction with respect to said tubular catheter.

6. The catheter insertion device of claim 5, further comprising:
an elongated slot in said outer housing, said elongated slot having a narrow proximal portion and a widened distal portion;
wherein said actuator handle is movable with respect to said elongated slot, such that said narrow proximal portion of said elongated slot constrains said actuator handle to move in a longitudinal direction to selectively advance said safety guidewire out through said tubular access needle in a distal direction and said widened distal portion allows said actuator handle to move in a lateral direction to actuate withdrawal of said safety guidewire and said tubular access needle in a proximal direction with respect to said tubular catheter.

7. The catheter insertion device as in claim 1, wherein said safety guidewire has a distal portion formed into a spiral curve wherein said spiral curve of said safety guidewire comprises a first spiral rotation and a second spiral rotation, said first spiral rotation being of a smaller diameter than said second spiral rotation.

8. The catheter insertion device of claim 7, wherein said first spiral rotation of said spiral curve of said safety guidewire is approximately coplanar with said second spiral rotation.

9. The catheter insertion device of claim 1, wherein said safety guidewire comprises a proximal portion and a distal portion, said proximal portion having a diameter that is greater than a diameter of said distal portion.

10. The catheter insertion device of claim 9, wherein said a distal portion of said safety guidewire is formed into a spiral curve.

11. The catheter insertion device of claim 1, wherein said safety guidewire is formed from a superelastic Nickel-Titanium alloy.

12. The catheter of claim 1, wherein the proximal hub has an interior divided into a distal chamber and a proximal chamber by a septum, wherein the wiping element is at a proximal end of the proximal chamber.

13. The catheter insertion device of claim 1, wherein the wiping element comprises an absorbent material that absorbs blood from surfaces of the needle and guidewire as they are withdrawn.

14. The catheter insertion device of claim 1, wherein the wiping element comprises an elastomeric membrane.

15. A method for inserting a catheter into a patient, comprising:
providing a catheter insertion device including an outer housing, an actuator mechanism, a tubular access needle attached to a needle carrier that is slidable with respect to said outer housing, a tubular catheter having a hub releasably attached at a distal end of said outer housing and positioned coaxially around said tubular access needle, a safety guidewire sized and configured to be advanced through said tubular access needle;
inserting a distal end of said tubular access needle into the patient;
actuating said actuator mechanism to advance said safety guidewire out through said tubular access needle in a distal direction;
advancing a distal end of said tubular catheter over the guidewire into the patient;
actuating said actuator mechanism to withdraw said safety guidewire and said tubular access needle through a septum in the hub in a proximal direction with respect to said tubular catheter to open an interior of the hub to receive blood; and
removing blood from surfaces of the tubular access needle and the guidewire by passing the needle and guidewire through a wiping element on a proximal side of the septum.

16. The method of claim 15, wherein, actuating said actuator mechanism releases a compressed spring disposed coaxially over the tubular catheter and the safety guidewire to engage the needle carrier to withdraw the needle and the guidewire from the catheter.

17. The method of claim 15, further comprising:
releasing said tubular catheter from said distal end of said outer housing.

18. The method of claim 15, wherein a distal portion of said safety guidewire is initially constrained in a straightened configuration within said tubular access needle; and wherein said distal portion of said safety guidewire assumes a spiral curve configuration upon advancement of said safety guidewire through said tubular access needle in a distal direction.

19. The method of claim 15, further comprising rotating a thumbwheel with respect to said outer housing to selectively advance said safety guidewire through said tubular access needle in a distal direction.

20. The method of claim 15, wherein the wiping element comprises an absorbent material that absorbs blood from surfaces of the needle and guidewire as they are withdrawn.

21. The method of claim 15, wherein the wiping element comprises an elastomeric membrane.

22. A catheter comprising:
a tubular catheter body having a proximal end;
a proximal huh attached to the proximal end of the tubular catheter body, said proximal hub having an interior chamber and a septum for passing an access needle and a guidewire on a proximal side of the interior chamber; and
a wiping element at a proximal side of the septum,
wherein the guidewire or access needle can pass through the wiping element and into the catheter and blood spatter can collect within the chamber as the needle or guide wire is withdrawn from the catheter, wherein the wiping element comprises an absorbent material disposed and the septum comprises an elastomeric membrane.

23. The catheter as in claim 22, further comprising a sidearm connector attached to the proximal hub to receive blood from the interior.

24. A system comprising the catheter of claim 22 in combination with a catheter insertion device comprising:
   an outer housing releasably attached to the proximal hub;
   a tubular access needle positioned coaxially within the outer housing attached to a needle carrier, wherein said needle carrier is slidable with respect to said outer housing and passes through the septum and wiping element of the proximal hub;
   a safety guidewire sized and configured to be advanced through said tubular access needle;
   an actuator mechanism configured to selectively advance said safety guidewire out through said tubular access needle in a distal direction and subsequently to simultaneously withdraw said safety guidewire and said tubular access needle in a proximal direction with respect to said tubular catheter.

25. The catheter insertion device as in claim 24, wherein said actuator mechanism compresses a compression spring located at a distal end of the housing coaxially over the tubular access needle and safety guidewire and an interlock which can be selectively released to allow the compression spring to elongate to simultaneously withdraw said safety guidewire and said tubular access needle.

26. The catheter insertion device as in claim 24, wherein said safety guidewire has a distal portion formed into a spiral curve wherein said spiral curve of said safety guidewire comprises a first spiral rotation and a second spiral rotation, said first spiral rotation being of as smaller diameter than said second spiral rotation.

27. The catheter insertion device of claim 26, wherein said first spiral rotation of said spiral curve of said safety guidewire is approximately coplanar with said second spiral rotation.

28. The catheter insertion device of claim 24, wherein said safety guidewire comprises a proximal portion and a distal portion, said proximal portion having a diameter that is greater than a diameter of said distal portion.

29. The catheter insertion device of claim 28, wherein said as distal portion of said safety guidewire is formed into a spiral curve.

30. The catheter insertion device of aim 24, wherein said safety guidewire is formed from a superelastic Nickel-Titanium alloy.

* * * * *